United States Patent [19]

Korwin et al.

[11] 4,424,034

[45] Jan. 3, 1984

[54] ARRANGEMENT FOR, METHOD OF, AND DEVICE FOR USE IN TAKING DENTAL IMPRESSIONS AND IN RESTORING TEETH

[76] Inventors: Paul Korwin, 150-09 77th Ave., Flushing, N.Y. 11367; Robert Korwin, 2300 Walnut St., Philadelphia, Pa. 19103

[21] Appl. No.: 503,066

[22] Filed: Jun. 10, 1983

[51] Int. Cl.³ .............................................. A61C 9/00
[52] U.S. Cl. ........................................ 433/40; 433/41
[58] Field of Search .......................... 433/60, 41; 47/9

[56] References Cited

U.S. PATENT DOCUMENTS

3,304,608  2/1967  Frohnecke ............................ 433/60
3,357,104  12/1967  Greene et al. ........................ 433/40
3,951,294  4/1976  Wilson ..................................... 47/9

Primary Examiner—Robert Peshock
Attorney, Agent, or Firm—Kirschstein, Kirschstein, Ottinger & Cobrin

[57] ABSTRACT

A ring-like adjustment member having a plurality of adjustable elements is mounted in a tooth-encircling relationship with a prepared tooth having a finish line. Each element is adjustably movable so that its leading edges may be moved toward an attachment line defined by the neck of the tooth and its immediately adjacent gingival tissue below the visible gum line. The leading edges, after adjustment, define an impression line whose contour resembles the contour of the finish and/or attachment lines. Accurate custom-made impressions of the prepared tooth may be obtained. The adjustment member may also be mounted on the prepared tooth to assist in the formation of a temporary crown, and may further be mounted as a readily removable matrix on a tooth requiring filling.

31 Claims, 8 Drawing Figures

ARRANGEMENT FOR, METHOD OF, AND DEVICE FOR USE IN TAKING DENTAL IMPRESSIONS AND IN RESTORING TEETH

BACKGROUND OF THE INVENTION

1. Field of the Invention

This invention generally relates to dental techniques for restoring teeth and, more particularly, to an arrangement for and method of taking dental impressions of a tooth to be restored, as well as to a novel dental device for use in taking accurate custom-made impressions even below the visible gum line at the neck of the tooth.

2. Description of the Prior Art

Dental techniques for restoring and treating teeth are well known. See, for example, U.S. Pat. Nos. 2,958,946, 3,151,393 and 3,760,502. In many tooth restorative procedures such as for making crowns, caps, overlays and inlays, a dental impression of the tooth to be restored is taken. The dental impression is a molded cavity that is used by a dental laboratory to manufacture an exact replica of the tooth. The better the replica, the better its fit will be in the patient's mouth.

One of the more prevalent techniques currently practiced by dentists in taking dental impressions of a prepared tooth which is to receive a prosthetic crown is to select an appropriately sized hollow impression tube, to position the tube about the prepared tooth, to push the tube downwardly onto the tooth to achieve a snug fit, to repeatedly attempt to shape the lower end of the tube to try to match the contour of the finish line defined by the edge of the prepared tooth or the attachment line defined by the neck of the tooth and its immediately adjacent gingival tissue below the visible gum line, and to introduce a settable impression substance into the interior of the tube. Once the impression substance has sufficiently set or hardened, the tube with the substance contained therein can be removed from the tooth for further work.

This general procedure has not proven to be altogether satisfactory, not only because the fit of the tube to the tooth at the attachment line at the neck of the tooth below the visible gum line is not accurate, but also because of the labor-intensive and time-consuming nature of the entire procedure. Specifically, after the tooth has been prepared, e.g. by grinding, the dentist must first estimate the size of the prepared tooth, and then select the appropriately sized tube from a plurality of differently sized tubes. This may take one, or usually more, attempts to correctly fit the tube over the periphery of the tooth. Thereupon, the dentist pushes the impression tube downwardly on the tooth past the finish line, i.e. the circumferential junction or shoulder between the upper prepared portion of the tooth and the lower unprepared portion of the tooth. The finish line may be above or below the visible gum line, i.e. the exterior visible line of gingival tissue which circumferentially surrounds the tooth. Frequently, the finish line is below the visible gum line and is uneven, i.e. the finish line varies in height along the circumferential direction and can rise or fall on the order of several millimeters in the generally vertical direction. The finish line may even, in some cases, extend as far downwardly as the attachment line, i.e. the circumferential line defined by the neck of the tooth and its immediately adjacent gingival tissue below the aforementioned visible gum line. As with the finish line, the attachment line is uneven and also typically varies several millimeters in height along the circumferential direction. The contour of the attachment line varies from tooth to tooth, as well as from patient to patient, and is not readily visible or accessible to the dentist because it is below the visible gum line.

In accordance with this prior art procedure, the dentist next attempts to shape the lower circular end of the cylindrical impression tube, which is typically constituted of copper, to match the contour of the uneven attachment line in order to attempt to take an accurate impression below the gum line, and particularly in the vicinity of the non-readily-visible/accessible region of the attachment line. A pointed curved instrument, frequently called an explorer, is inserted into the space between the tooth and its surrounding gingival tissue and is used by the dentist to feel how far the copper tube can be pushed downwardly without tearing the gingival tissue at the attachment line. The dentist mentally estimates the depth of insertion of his explorer at as many points around the tooth as he can memorize at one time, and then, based on this rather crude memorized exploration, the dentist blindly attempts to trace or outline the contour of the attachment line on the lower end of the copper tube. The dentist then uses a cutting instrument to cut the lower end of the tube along his traced outline so that the lower edge of the tube attempts to duplicate the contour of the attachment line.

After cutting the tube, the dentist checks the fit of the cut edge of the tube by pushing the latter downwardly on the tooth and again exploring by feel just how far the tube can be pushed beyond the finish line without tearing the gingival tissue at the attachment line. Further adjustments in the shaping of the tube can be made by repetitively pushing the tube onto the tooth, reexploring the neck region, tracing corrected outlines on the tube, recutting the tube, and refitting the tube until a more or less acceptable contour and fit are achieved. This is obviously a very crude, awkward and time-consuming operation.

After completing the cutting operation, the next step in the prior art dental procedure is to fill the tube with a primary settable impression substance such as a cold-cure acrylic material and then, after an initial impression is taken, some of the acrylic material is removed to allow room for a more accurate secondary impression substance. During the setting of both the primary and secondary impression substances, the contour and fit of the tube cannot be changed.

SUMMARY OF THE INVENTION

1. Objects of the Invention

Accordingly, it is a general object of this invention to overcome the aforementioned drawbacks of the prior art dental techniques of taking dental impressions.

It is an object of this invention to take an accurate custom-made dental impression of a prepared tooth, particularly in the non-readily accessible/visible region of its attachment line below the visible gum line.

It is another object of this invention to easily and reliably obtain an accurate fit of a dental impression-taking device about the entire periphery of the neck region of a prepared tooth.

It is yet another object of this invention to eliminate the guesswork and memorization involved in attempting to shape an impression-taking device.

It is a further object of this invention to eliminate the procedure of repetitively using an explorer to estimate the depth of the attachment line.

It is a still further object of this invention to eliminate the procedure of cutting and recutting excess unwanted material from an impression-taking device.

It is another object of this invention to eliminate tissue tearing and injury to a patient by pushing an inexactly fitting impression-taking device onto a tooth and into the gingival tissue at the attachment line, particularly during the intermediate stages of shaping the impression-taking device.

It is yet another object of this invention to considerably reduce the time and labor involved in fitting an impression-taking device and taking a dental impression.

It is a further object of this invention to eliminate inexactness and waste in precutting impression-taking devices which then may not fit a particular patient.

It is a still further object of this invention to shape an impression-taking device into a contour resembling, or closely matching, or exactly matching the finish or attachment lines using finger pressure alone.

It is another object of this invention to change the shape of an impression-taking device into a contour resembling the finish or attachment lines even during setting of the subsequently introduced settable substances.

It is yet another object of this invention to eliminate the necessity for stocking a plurality of differently sized impression-taking devices.

It is a further object of this invention to provide a novel arrangement for, a method of, and a device for use in taking dental impressions which create an impression line which resembles, closely matches and, in some cases, exactly matches the contour of the finish or attachment lines in a highly and finely adjustable, easy to perform, cost effective and labor saving manner.

It is a still further object of this invention to minimize excessive discomfort to the patient, and to minimize the amount of time the patient is required to sit in the dental chair during the impression-taking procedure.

2. Features of the Invention

In keeping with these objects and others which will become apparent hereinafter, one feature of the invention resides, briefly stated, in an arrangement for, a method of, and a device for use in taking dental impressions of a prepared tooth having a finish line.

The device comprises a tooth-encircling adjustment member having a plurality of elongated adjustable elements mounted in a surrounding relationship with the prepared tooth. The adjustable elements are adjustably movable along the direction of their elongation, e.g. in a generally vertically downward direction in a clearance space between the tooth and its surrounding gingival tissue. The adjustable elements have leading edges, e.g. their lower edges, as considered in the direction of downward movement, which are adjustably movable toward the attachment line, i.e. the circumferentially extending uneven non-readily-visible/accessible contoured line defined by the neck region of the tooth and its immediately adjacent gingival tissue below the visible gum line. The leading edges, after their adjustment, which is preferably manually performed by the dentist by exerting finger pressure on the trailing edges of the adjustable elements until the dentist feels resistance to further downward movement, together define a circumferentially extending impression line whose contour resembles the contour of one of said lines. Preferably, although not necessarily, the leading edges are moved to the attachment line itself. However, it is also within the spirit of this invention that the leading edges are moved to a position short of the attachment line and, in some cases, to just past the finish line, i.e. the circumferential line or junction between the prepared and unprepared portions of the tooth and, in still other cases, to the finish line itself and, in yet other cases, to just short of the finish line. In all of these situations, the leading edges of the adjustable elements are pushed downwardly to the extent dictated by the prevailing dental circumstances so that the contour of the resulting impression line resembles or, in some cases, closely matches or, in ideal cases, exactly matches the contour of the finish line and/or the attachment line.

Hence, in accordance with this invention, accurate custom-made impressions of the prepared tooth may be taken because the uneven and non-readily-visible/accessible finish or attachment lines may be duplicated to the maximum extent possible by the expedient of adjusting the position of the adjustable elements about the circumference or periphery of the tooth. It is no longer necessary for the dentist to use an explorer, or to estimate the depth of the attachment line, or to memorize the depths around the tooth, or to trace an outline around an impression-taking copper tube, or to cut the tube, or to refit the cut tube on the tooth, or to repeat all of the above steps for as long as it takes or to the extent that the dentist's mechanical skills permit him to fabricate and position an accurately fitting impression-taking device. This invention substantially minimizes the very time-consuming and labor-intensive and essentially crude prior impression-taking techniques while, at the same time, substantially spares the patient from injury and excessive discomfort. The human patient will not have to sit in the dental chair for long periods of time to complete this procedure, thereby helping to minimize any fear that the patient may have. The resulting fit of the prosthetic replica or crown that will ultimately be made will be much improved in accordance with this invention.

Once a settable impression substance has been introduced into the interior of the device, the adjustable elements may, if necessary, still be adjusted in accordance with this invention. This continuing adjustability, even during the setting of the impression substance and up to final hardening of the same, has not heretofore been available to dentists and allows simultaneous filling and impression taking, and is of immense advantage in cases where the adjustable member shifts while the patient is waiting for the settable substance to harden.

In further accordance with this invention, it is no longer necessary to stock a plurality of differently sized impression-taking devices to select the most appropriately sized one for a particular dental situation. In accordance with this invention, the adjustable elements are interconnected in a mutually releasably interlocked manner and may be arranged in a coiled configuration so that they occupy a small amount of space. The coil may be unwound to form a band or strip of predetermined length, and the adjustable element at the end of the strip which is opposite to the free end thereof is released from interlocking engagement from the remainder of the coil. The strip is now closed upon itself in an annulus by bringing the adjacent elements at opposite ends of the strip into a close confronting relationship, and by connecting the released adjustable element into interlocking engagement with the pair of confronting elements to thereby form a ring-like adjustment member whose inner circumference closely matches the outer circumference or periphery of the prepared tooth which is to be encircled by the adjustment member in accordance with the method of this invention. In this way, the correctly sized adjustment member may be made to the appropriate size desired. It is also within the spirit of this invention to provide generally planar strips of different lengths and, of course, to provide preformed ring-like adjustment members of different circumferential sizes.

The adjustment member may also be used in other dental restorative techniques such as in aiding in the construction of fillings, and in the formation of temporary crowns.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figures 1, 2, 3:
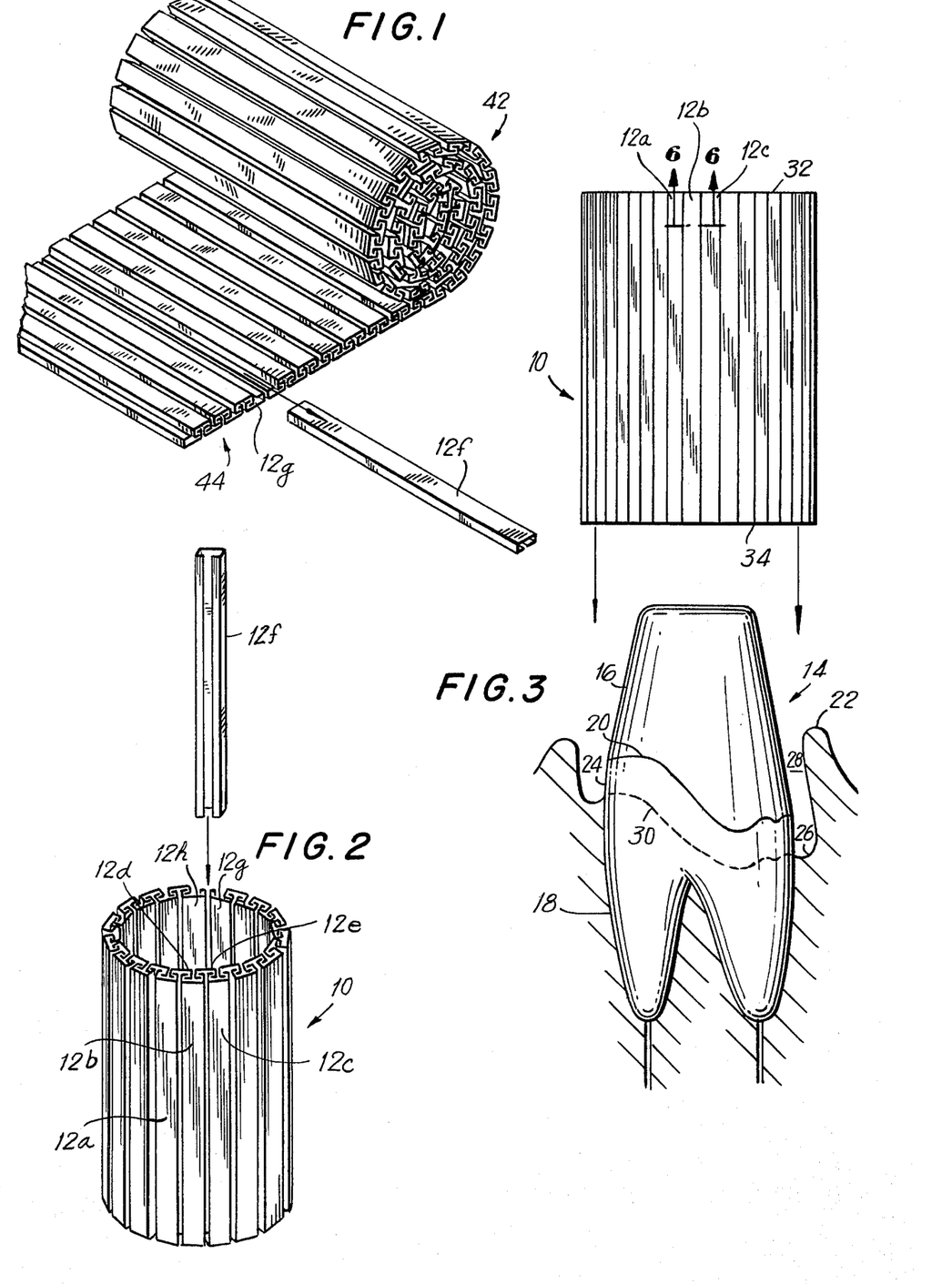
FIG. 1 is an enlarged perspective view of a coil of interconnected adjustable elements with one adjustable element removed to form a strip of a predetermined length.
FIG. 2 is an enlarged perspective view of a ring-like adjustment member being formed by the connection of the removed adjustable element of FIG. 1.
FIG. 3 is an enlarged front vertical view of the ring-like adjustment member of FIG. 2 being positioned on a prepared tooth.
Figure 4:
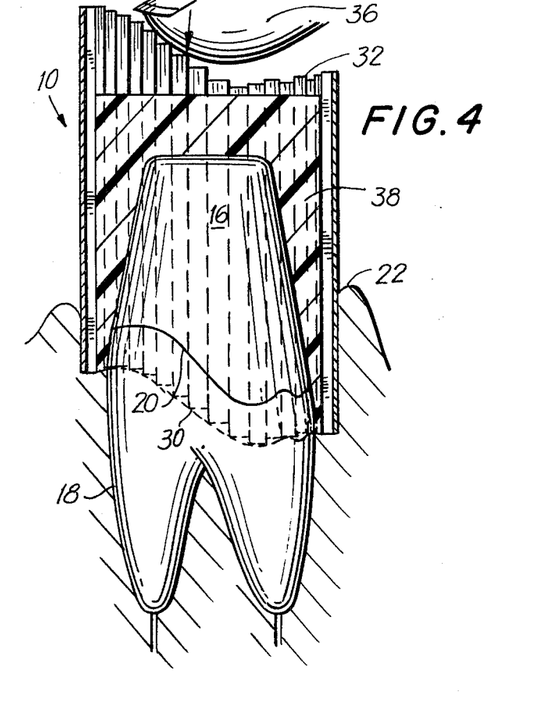
FIG. 4 is an enlarged partly sectioned vertical view of the adjustment member of FIG. 2 during adjustment and after introduction of a primary settable impression substance.
Figure 5:
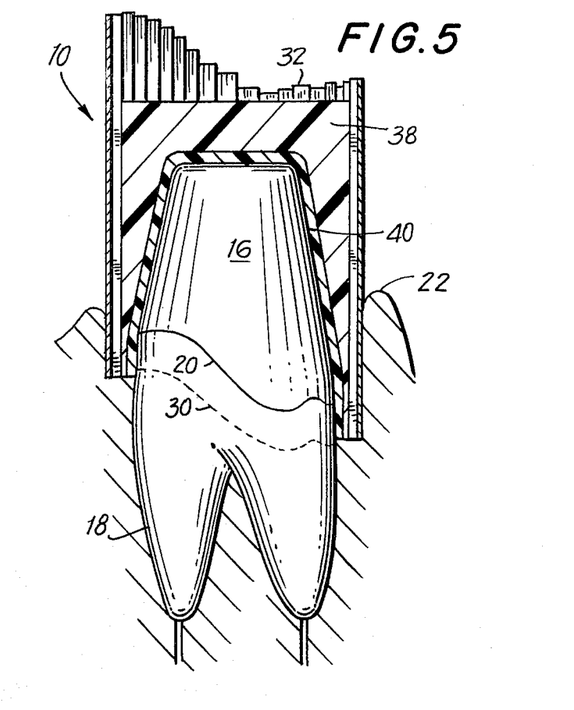
FIG. 5 is a view analogous to FIG. 4 after a secondary settable impression substance has been introduced into the adjustment member.

Referring now to the drawings in detail, reference numeral 10 generally identifies a tooth-encircling adjustment member having a plurality of elongated adjustable elements each identified by the reference numeral 12 followed by a letter suffix. As best shown in FIGS. 3-5, the adjustment member 10 is to be mounted on a tooth 14 so that the adjustable elements 12 surround the same.

Prior to mounting the adjustment member 10, the tooth 14 is prepared, typically by grinding the upper crown portion 16 of the tooth to form a frusto-conical shape. The lower root portion 18 of the tooth 14 remains unprepared, and the circumferentially extending junction or shoulder between the prepared portion 16 and the unprepared portion 18 is the finish line 20. The finish line 20 may be above or below, and is typically below, the visible gum line 22, i.e. the exterior visible line of gingival tissue which circumferentially surrounds the tooth. As shown in FIG. 3, the finish line 20 is uneven, and varies in height on the order of several millimeters circumferentially of the tooth. The contour of the finish line 20 depends, for the most part, on the mechanical grinding skill of the dentist and his treatment plan for the patient.

At the neck region 24 of the tooth, the circumferential line, which is defined by the neck and its immediately adjacent gingival tissue 26, is the attachment line 30. The attachment line 30, like the finish line 20, is uneven, and typically varies several millimeters in height along the circumferential direction. The contour of the attachment line 30 varies from tooth to tooth, as well as from patient to patient, and is not readily visible or accessible to the dentist because the attachment line 30 is below the visible gum line 22. The clearance or space 28 between the tooth and its surrounding gingival tissue is quite narrow and limits ready access to the neck region 24. The contour of the attachment line 30 need not, and typically does not, match the contour of the finish line 20. In some cases, the finish line may even extend downwardly to the attachment line.

In accordance with this invention, the adjustable elements 12 are arranged in an annulus to form a cylindrical ring or band whose side wall has an internal circumference that corresponds to the outer circumference of the prepared tooth, particularly at its widest part, so as to form a snug fit therewith when mounted thereon. Each adjustable element 12 is elongated in the vertical direction and is movable along said direction. As considered in the direction of downward vertical movement, each adjustable element 12 has an upper trailing edge at the upper open end 32 of the ring 10, and a lower leading edge at the lower open end 34 of the ring. By exerting pressure on the upper trailing edge of each element, e.g. finger pressure by the dentist, the lower leading edge of the respective element 12 can be adjustably moved to any desired position as detailed below.

Figure 6:
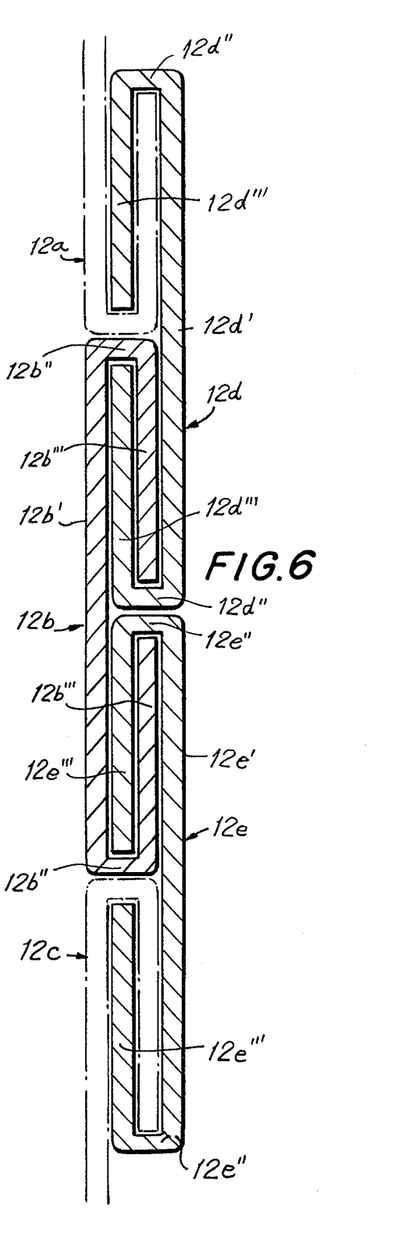
FIG. 6 is a greatly enlarged sectional view of the adjustable elements which are interconnected in a mutually sliding interlocking and partially overlapping relationship as taken on line 6—6 of FIG. 3.

The adjustable elements are preferably mounted in a sliding interlocked, and at least partially overlapping, relationship with each other. As best shown in FIG. 6 for the representative elements 12a, 12b, 12c, 12d and 12e, each element has a generally rectangularly C-shaped channel-like configuration. Thus, representative element 12b has a substantially planar base portion 12b', a pair of perpendicular border portions 12b'' at opposite lateral sides of the base portion 12b', and a pair of offset flange portions 12b''' which lie in a mutual plane that is parallel to the plane of the base portion 12b'. The space between the offset flange portions and the base portion defines a channel.

Representative elements 12d and 12e similarly have base portions 12d', 12e', border portions 12d'', 12e'', and offset flange portions 12d''', 12e''', respectively.

As shown in FIG. 6, elements 12d and 12e interlockingly engage element 12b by slidably inserting the lower offset flange 12d''' and the upper offset flange 12e''' into the channel between the offset flange portions 12b''' and the base portion 12b'. The lower border portion 12d'' and the upper border portion 12e'' are received through the open side of the C-shaped element 12b.

In analogous manner, representative elements 12a and 12c and, in turn, the remaining elements of the ring, are interlockingly connected to the elements 12b, 12d and 12e.

The clearances between the elements are quite small, and are sufficient to provide a frictional sliding fit. If necessary, the elements may be applied with a low-friction coating, or be constituted of an anti-friction material, to minimize friction.

The element 12a partially overlaps element 12d, which in turn partially overlaps element 12b, which in turn partially overlaps element 12e, which in turn partially overlaps element 12c, and so on. The overlapping of the adjustable elements permits the lower edges to define a more or less continuous lower end for the ring 10.

Each element may be constituted of a metal or a synthetic plastic material. Currently, semi-hard brass, stainless steel, or copper is preferred. Low-friction coatings such as fluorocarbon materials preferably are applied to the interior sliding surfaces of the elements. Each element is very narrow so as to fit into the narrow space 28 (see FIG. 3) between the tooth and its surrounding gingival tissue. The wall thickness of each element may vary typically from about 0.02 millimeters to about 0.10 millimeters, and preferably is about 0.05 millimeters. The overall thickness of each individual element, in a preferred embodiment, is on the order of 0.18 millimeters, and the overall thickness of the internal locking elements, i.e. the side wall of the ring, is on the order of 0.24 millimeters. Clearances between slidable surfaces is about 0.01 millimeters. The width of each element as considered in the circumferential direction may vary from about 0.5 millimeters to about 2 millimeters, and is currently preferred to be about 1 millimeter.

Each element overlaps the adjacent element by about one-half to constitute a width in the preferred embodiment of about 0.5 millimeters. The length of each element may vary from about 5 millimeters to about 20 millimeters and, in a preferred embodiment, is typically about 14 millimeters. Experience and tests with teeth have shown that the preferred dimensions listed above will provide satisfactory results without injuring the gingival tissue, as well as providing adequate rigidity to the ring and easy adjustability.

It is contemplated that localized and permanent deformation of the ring about the periphery of the tooth is desirable, and the very thin and miniature dimensions described above facilitate such localized deformation.

Referring now to FIG. 4, after the ring 10 has been positioned about the prepared tooth, the dentist uses his finger 36 to manually urge the elements downwardly toward the attachment line 30 until resistance is manually felt by the dentist. Ideally, the elements 12 are pushed all the way down to the attachment line so that the lower leading edges of the elements together define and generally lie along an impression line whose circumferential contour substantially matches the contour of the attachment line 30. An exact match is not achievable due to the horizontal lower linear edge of each element. However, if a more exact match is required, the dentist can remove the ring 10 from the tooth after an initial adjustment has been made, and trim the lower leading edges into a continuous curvilinear shape which exactly matches the contour of the attachment line 30. In some dental situations, this ideal case is not achieved, and the leading edges are adjusted to positions just short of the attachment line. In other cases, the leading edges may only be adjusted to just past the finish line 20, or perhaps only to the finish line itself, or perhaps, in yet other situations, to just short of the finish line. In all of these cases, the leading edges have been pushed as far downwardly as the dental circumstances will permit, while at the same time not injuring the patient. The overlapping orientation of the elements permits the resulting impression line to be more or less continuous, particularly after the lower leading edges have been trimmed. The impression line matches the periphery of the tooth as far down as the dental circumstances permit and, hence, will result in a highly accurate dental impression. The adjustment procedure can be successfully performed in just a few seconds.

After adjustment of all the elements of the ring, a primary settable dental impression material 38, such as a quick-setting cold-cure methyl methacrylate, is prepared and introduced into the interior of the ring. The primary material may be placed into the ring through its open upper end 32 without disturbing the adjusted relationship of the elements. The settable material does not readily flow from the interior of the ring to its exterior because of the maze-like path formed by the interconnecting elements, as best shown in FIG. 6. As a practical matter, the maze-like path prevents any leakage of the settable material through the side wall of the ring. The primary material 38 will harden in time and, while it hardens, the elements can still be adjusted, if necessary.

When the primary material 38 is sufficiently hardened, the ring and the hardened material 38 are removed as a unit from the tooth. A small amount of primary material 38 is uniformly removed from the interior surface thereof by grinding it with a dental hand-piece.

Now a secondary settable dental impression material 40, such as silicone rubber, polyether material, etc., is prepared and introduced into the removed portion of primary material. This secondary material has characteristics which permit a more accurate impression, as compared to the primary material. The ring with the still-unset secondary material is now mounted back on the tooth and, after setting, is again removed. The resulting dental impression is an accurate custom-made one which has duplicated the prepared tooth, and particularly the area in the vicinity of the finish line at the non-readily accessible/visible neck region thereof, and especially at the attachment line thereof. The dental laboratory will now prepare a prosthetic tooth or crown from the impression in a conventional manner.

To fit teeth of different sizes, a plurality of different sized cylindrical rings 12 may be provided. The dentist will then select the appropriately sized ring for a particular tooth. It is also within the spirit of this invention to have the dentist form the ring from a planar or coiled strip or band of adjustable elements. Thus, as shown in FIG. 1, a coil 42 of adjustable elements 12 may be unwound, and one of the adjustable elements, e.g. 12f, may be slid off the coil 42 in the direction of the illustrated arrow to form a planar strip or band 44 of a predetermined length.

Thereupon, as shown in FIG. 2, the band 44 of predetermined length is formed into a cylindrical shape by bringing the adjustable elements 12g and 12h, which are located at opposite ends of the band 44, into a close confronting spaced relationship with each other. The removed element 12f may now conveniently serve as a joining element by sliding it in the direction of the illustrated arrow over the adjacent offset flange portions of the end elements 12g and 12h. An integrated ring-like adjustment member 10 has just been conveniently constructed with an inner circumference that corresponds to the outer circumference of the prepared tooth in question.

Rather than providing a coil, the elements may be initially provided in planar strips of different lengths, or, as mentioned above, may be provided as cylindrical tubes of different diameters.

The above described method of taking a dental impression can be performed in a relatively short time. If desired, the dentist may optionally wish to trim the upper trailing edges of the elements after the latter have been adjusted in order to make the patient more comfortable and provide room for the bite and to simultaneously form a cast imprint of the latter. By optionally trimming the upper edges, the patient's comfort will be enhanced during this procedure.

This invention is applicable not only to human teeth, but also to animal teeth so as to assist a veterinarian.

In addition, the elements need not be mutually interlockingly engaged with each other in an overlapping relationship, but may also be mounted for downward movement on a ring-like support in which the various adjustable elements are circumferentially spaced apart from one another. However, in this latter case, due to the staggered relationship of the lower edges of the spaced-apart elements, the attachment line will not be duplicated to the same extent as can be achieved with the overlapping elements described herein.

It is also preferable if each adjustable element is formed of a resilient material so as not only to permit localized and permanent deformation, but also to permit the adjustable element to yield radially outwardly in order to avoid injuring the patient.

The adjustment member can be used in many dental restorative techniques other than in taking dental impressions. For example, the adjustment member can be used in the formation of temporary crowns on a tooth awaiting a permanent crown. In the current state of the art, a temporary acrylic crown is mounted on a prepared tooth by initially pushing an appropriately sized copper tube downwardly on the tooth. The lower leading end of the tube is then traced and cut in the above-described crude, awkward and time-consuming manner in order to attempt to match the finish line. The upper trailing end of the tube is reduced in height by cutting, and is then further formed by cutting with a series of small rectangular cutouts to form a serrated upper edge. A settable substance such as methyl methacrylate acrylic, preferably tooth-colored, is then applied over the prepared tooth with the cut tube remaining in place. The dentist shapes the acrylic into an approximate tooth-like shape with his fingers, and the patient is instructed to bite down and into the acrylic in order to make its occlusal surface conform to the opposing tooth surface. Once the acrylic has hardened, it is removed from the tooth, ground into a more tooth-like shape, polished, readjusted to fit back on the prepared tooth, and cemented thereon over the cut tube to serve as a temporary crown. The acrylic in the cutouts helps to anchor the temporary crown in place.

Figures 7, 8:
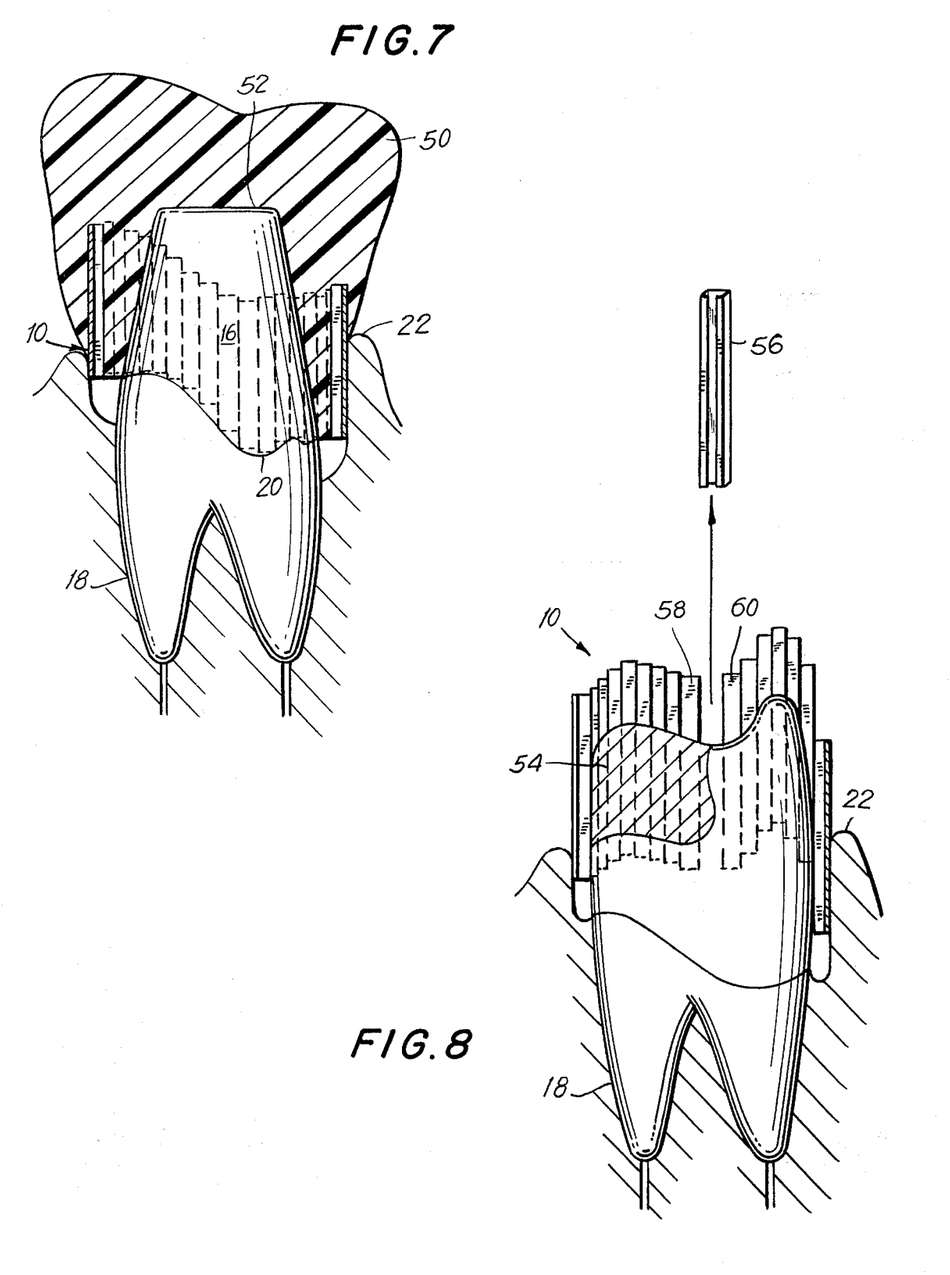
FIG. 7 is an enlarged perspective view of a reduced height adjustment member mounted as a temporary crown on a prepared tooth.
FIG. 8 is an enlarged perspective view of the adjustment member of FIG. 2 being removed from a filled tooth after serving as a matrix therefor.

In accordance with the present invention, as shown in FIG. 7, an adjustment member of reduced height is mounted on the prepared tooth and, as described above, the adjustable elements are slid downwardly until their leading edges define a contour which resembles the contour of the finish line. The tracing and cutting of the lower end of the prior art tube is thereby eliminated. In addition, the cutting of the upper end of the prior art tube into a serrated edge is likewise eliminated because, after adjustment of the adjustable element, the trailing edges of the elements are staggered and, in effect, form anchoring surfaces for the acrylic 50 which is thereupon applied over the adjustable member that is left in place about the tooth. The reduced height adjustment member, i.e. whose trailing edges lie between the finish line and the crown or upper prepared surface 52 of the tooth, can be finished in various reduced heights, e.g. on the order of 4-5 mm.

The temporary crown consisting of the acrylic 50 and the adjustment member forms a hard, durable structure which resists fracture of the acrylic. The adjustment member reinforces the prepared tooth all along the finish line and protects the prepared tooth itself from breaking. The acrylic need not be constituted of as thick or massive material as in the prior art due to the reinforcement provided by the adjustment member, and this feature prevents overbulking of the crown margin which can be deleterious to the health of the gingival tissue.

The use of the adjustment member for making a temporary crown reduces the time necessary for implementing this procedure. If the adjustment member is made of a synthetic plastic material, then this will facilitate the bonding between the plastic adjustment member and the acrylic. If the adjustment member is made of a stainless steel, then this will tend to eliminate corrosion and staining and is of advantage when the temporary crown is to be left in the mouth for a long time. The stainless steel adjustment member can be sterilized and reused if desired.

The adjustment member can be used as a matrix in another dental restorative technique such as in filling large cavities. In the current state of the art of constructing large fillings for teeth, a copper tube is fitted over a badly broken-down tooth, i.e. one requiring a large filling, such that the cavity to be filled is located within the interior of the tube. The lower end of the tube is then traced and cut in the above-described crude, awkward and time-consuming manner in order to extend past the cavity and to try to prevent the lower tube end from cutting into or otherwise impinging on the gingival tissue. A filling settable material such as dental amalgam 54 is then compacted into the cavity and, when the amalgam has set, the tube is removed. Sometimes the tube must be cut off the tooth with a high-speed drilling instrument which may lead to injury of the gingival tissue. The upper end of the tube may be trimmed to fit the patient's bite if the tube is to stay on until a subsequent dental visit.

In accordance with the present invention, as shown in FIG. 8, an adjustment member is used as a matrix band by snugly mounting it about the tooth, and by adjusting the adjustable elements until their leading edges are located beyond the broken-down sections of the tooth. The dental amalgam 54 may then be compacted in the cavity. The cutting of the lower tube end has been eliminated. In addition, the adjustment member is not cut off the tooth, but can be easily and quickly unwrapped therefrom by first removing one adjustable element 56, and then by urging the adjustable elements 58, 60 at opposite ends of the adjustment member away from each other to thereby open up the adjustment member. The removed adjustment member 56 is easily sterilized and may be reused.

The unwrapping of the adjustment member is particularly advantageous, because this feature tends to eliminate the prior art problem of fracturing a filling during removal of the matrix band. When a conventional matrix tube is removed from a tooth, a small part of the filling, particularly a recent one, tends to fracture due to the leverage exerted on the still-weak filling material. The unwrapping of the adjustment member in the circumferential direction after removal of an adjustable element reduces the leverage force exerted on a recent, fragile filling and prevents such fracture.

It will be understood that each of the elements described above, or two or more together, may also find a useful application in other types of constructions differing from the types described above.

While the invention has been illustrated and described as embodied in an arrangement for, method of, and device for use in taking dental impressions, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A device for use in taking dental impressions of a prepared tooth having a finish line, comprising:
   a tooth-encircling adjustment member having a plurality of elongated adjustable elements mounted in a surrounding relationship with the prepared tooth, said adjustable elements being adjustably movable along the direction of their elongations in a space between the tooth and the surrounding gingival tissue, said adjustable elements having leading edges as considered in the direction of movement which are adjustably movable toward a circumferentially extending attachment line defined by the neck of the tooth and its immediately adjacent gingival tissue, said adjusted leading edges together defining a circumferentially extending impression line whose contour resembles the contour of one of said lines, whereby accurate custom-made impressions of the prepared tooth may be taken.

2. The device as defined in claim 1, wherein the adjustment member is arranged in a hollow cylindrical configuration having opposite open ends, and wherein the adjustable elements constitute the side wall of the cylindrical adjustment member.

3. The device as defined in claim 1, wherein each adjustable element is mounted for sliding movement along the elongated direction.

4. The device as defined in claim 1, wherein each adjustable element is at least partially overlapped in the circumferential direction by another adjustable element.

5. The device as defined in claim 1, wherein each adjustable element has a generally C-shaped configuration, and wherein the adjustable elements are interlocked in a sliding relationship.

6. The device as defined in claim 1, wherein the leading edges of the adjustable elements are adjustably moved to the attachment line so that the contour of the impression line closely matches the contour of the attachment line.

7. The device as defined in claim 1, wherein each adjustable element has a narrow overall thickness on the order of 0.2 mm, a length on the order of 14 mm, and a width on the order of 1 mm.

8. The device as defined in claim 1, wherein the adjustment member has an initial generally planar configuration which is formable into a tooth-encircling configuration.

9. An arrangement for taking dental impressions of a prepared tooth having a finish line, comprising:
   (a) a tooth-encircling adjustment member having a plurality of elongated adjustable elements mounted in a surrounding relationship with the prepared tooth, each adjustable element having a leading edge as considered in the direction of adjustment;
   (b) means for adjustably moving the adjustable elements along the direction of their elongations in a space between the tooth and the surrounding gingival tissue so that their leading edges are adjustably moved toward a circumferentially extending attachment line defined by the neck of the tooth and its immediately adjacent gingival tissue, said adjusted leading edges together defining a circumferentially extending impression line whose contour resembles the contour of one of said lines; and
   (c) means for introducing a settable impression substance into the interior of the adjustment member and about the tooth to take an accurate custom-made impression of the same.

10. The arrangement as defined in claim 9, wherein the moving means includes means for mounting the adjustable elements for sliding movement relative to one another.

11. The arrangement as defined in claim 9, wherein each adjustable element is at least partially overlapped in the circumferential direction by another adjustable element.

12. The arrangement as defined in claim 9, wherein each adjustable element is mounted in an interlocking sliding relationship with another adjustable element.

13. The arrangement as defined in claim 9, wherein the leading edges of the adjustable elements are adjustably moved to the attachment line so that the contour of the impression line closely matches the contour of the attachment line.

14. The arrangement as defined in claim 9; and further comprising means for removing a portion of the impression substance after setting thereof and after displacement from the prepared tooth, and means for introducing a settable impression material into the removed portion of the impression substance prior to replacement on the prepared tooth.

15. The arrangement as defined in claim 9; and further comprising means for forming the tooth-encircling adjustment member in an annular configuration from a generally planar initial configuration.

16. A method of taking dental impressions of a prepared tooth having a finish line, comprising the steps of:
   (a) surrounding the prepared tooth with an adjustment member having a plurality of elongated adjustable elements each having a leading edge as considered in the direction of adjustment;
   (b) adjustably moving the adjustable elements along the direction of their elongations in a space between the tooth and the surrounding gingival tissue so that their leading edges are adjustably moved toward a circumferentially extending attachment line defined by the neck of the tooth and its immediately adjacent gingival tissue, said adjusted leading edges together defining a circumferentially extending impression line whose contour resembles the contour of one of said lines; and (c) introducing a settable impression substance into the interior of the adjustment member and about the tooth to take an accurate custom-made impression of the same.

17. The method as defined in claim 16, wherein said moving step is performed by manually pushing the adjustable elements at their trailing edges.

18. The method as defined in claim 16, wherein said moving step is performed while the impression substance is setting.

19. The method as defined in claim 16, wherein said moving step is performed by manually sliding the adjustable elements relative to one another until the leading edges are adjustably moved to the attachment line so that the contour of the impression line closely matches the contour of the attachment line.

20. The method as defined in claim 16; and further comprising the step of removing a portion of the impression substance after setting thereof and after displacement from the prepared tooth, and the step of introducing a settable impression material into the removed portion of the impression substance prior to replacement on the prepared tooth.

21. The method as defined in claim 16, wherein said surrounding step is performed by forming the adjustment member in an annular configuration from a generally planar initial configuration.

22. The method as defined in claim 21, wherein said forming step includes the steps of providing the adjustment member in a coil, unwinding the coil, removing a selected adjustable element from the unwound coil to select a predetermined length, shaping the unwound coil into an annular shape by positioning the adjustable elements at opposite ends of the unwound coil adjacent each other, and mounting the selected adjustable element onto the adjacently positioned adjustable elements.

23. A device for use in restoring a tooth, comprising:
a tooth-encircling adjustment member having a plurality of elongated adjustable elements mounted in a surrounding relationship with the tooth to be restored, said adjustable elements being adjustably movable along the direction of their elongations and having leading edges as considered in the direction of movement which are adjustably movable toward the root of the tooth.

24. The device as defined in claim 23, wherein the adjustment member surrounds a prepared tooth having a finish line and an upper prepared surface, and wherein the adjustment member is situated between the finish line and the upper prepared surface, and wherein the leading edges of the adjustable elements are adjustably movable toward the finish line to reinforce the latter in the construction of a temporary crown.

25. The device as defined in claim 23, wherein the adjustable member surrounds a tooth having a cavity to be filled, and wherein the leading edges of the adjustable elements are adjustably movable along the tooth to positions beyond the cavity to bound the latter.

26. An arrangement for restoring a tooth, comprising:
(a) a tooth-encircling adjustment member having a plurality of elongated adjustable elements mounted in a surrounding relationship with the tooth, each adjustable element having a leading edge as considered in the direction of adjustment;
(b) means for adjustably moving the adjustable elements along the direction of their elongations so that their leading edges are adjustably moved toward the root of the tooth; and
(c) means for applying a settable substance on the tooth with the adjustment member surrounding the same.

27. The arrangement as defined in claim 26, wherein the adjustment member surrounds a prepared tooth having a finish line and an upper prepared surface, and wherein the adjustment member is situated between the finish line and the upper prepared surface, and wherein the leading edges of the adjustable elements are adjustably movable toward the finish line to reinforce the latter in the construction of a temporary crown, and wherein the applying means is operative to apply the settable substance about at least a part of the exterior of the adjustment member to form the temporary crown.

28. The arrangement as defined in claim 26, wherein the adjustable member surrounds a tooth having a cavity to be filled, and wherein the leading edges of the adjustable elements are adjustably movable along the tooth to positions beyond the cavity to bound the same, and wherein the applying means is operative to apply the settable substance into the cavity bounded at least in part by the adjustment member.

29. A method of restoring a tooth, comprising the steps of:
(a) surrounding the tooth with an adjustment member having a plurality of elongated adjustable elements each having a leading edge as considered in the direction of adjustment;
(b) adjustably moving the adjustable elements along the direction of their elongations so that their leading edges are adjustably moved toward the root of the tooth; and
(c) applying a settable substance on the tooth with the adjustment member surrounding the same.

30. The method as defined in claim 29, wherein said surrounding step is performed by situating the adjustment member between a finish line and an upper prepared surface of a prepared tooth, and wherein said moving step is performed by moving the leading edges toward the finish line to reinforce the latter in the construction of a temporary crown, and wherein said applying step is performed by applying the settable substance about at least a part of the exterior of the adjustment member to form the temporary crown.

31. The method as defined in claim 29, wherein said surrounding step is performed by situating the adjustment member about a tooth having a cavity to be filled, and wherein said moving step is performed by moving the leading edges to positions beyond the cavity to bound the same, and wherein said applying step is performed by applying the settable substance into the cavity bounded at least in part by the adjustment member.

* * * * *